(12) United States Patent
Wolford

(10) Patent No.: US 6,978,648 B2
(45) Date of Patent: Dec. 27, 2005

(54) ACETABULAR REAMER LIPPING SYSTEM AND METHOD

(75) Inventor: Todd A. Wolford, Goshen, IN (US)

(73) Assignee: Symmetry Medical, Inc., Warsaw, IN (US)

( * ) Notice: Subject to any disclaimer, the term of this patent is extended or adjusted under 35 U.S.C. 154(b) by 161 days.

(21) Appl. No.: 10/353,546

(22) Filed: Jan. 29, 2003

(65) Prior Publication Data

US 2004/0144147 A1 Jul. 29, 2004

(51) Int. Cl.⁷ ................................................ B21D 3/02
(52) U.S. Cl. ........................ 72/74; 72/115; 72/124; 72/215; 606/81
(58) Field of Search .......................... 72/74, 75, 112, 72/115, 124, 125, 214, 215, 216, 217, 340, 379.2; 606/80, 81

(56) References Cited

U.S. PATENT DOCUMENTS

| | | | | |
|---|---|---|---|---|
| 1,461,853 A | * | 7/1923 | Kennedy | 72/74 |
| 4,811,632 A | | 3/1989 | Salyer | 76/101 |
| 4,909,059 A | * | 3/1990 | King | 72/217 |
| 5,116,165 A | | 5/1992 | Salyer | 407/54 |
| 5,302,234 A | | 4/1994 | Grace et al. | 156/640 |
| 5,499,521 A | * | 3/1996 | Luikart et al. | 72/157 |
| 5,709,688 A | | 1/1998 | Salyer | 606/81 |
| 5,968,049 A | | 10/1999 | Da Rold | 606/80 |
| 6,001,105 A | | 12/1999 | Salyer | 606/81 |
| 6,027,503 A | | 2/2000 | Khalili et al. | 606/81 |
| 6,129,732 A | | 10/2000 | Lechot | 606/80 |
| 6,168,600 B1 | * | 1/2001 | Grace et al. | 606/81 |

* cited by examiner

Primary Examiner—Ed Tolan
(74) Attorney, Agent, or Firm—Taylor & Aust, P.C.

(57) ABSTRACT

A lipping tool for lipping an acetabular reamer, the lipping tool comprising a bending form having a bending form curved surface and a bending form axis of rotation; and a pressure tool having a pressure tool curved surface adjacent to and complimentary with the bending form curved surface. The pressure tool has a pressure tool axis. The pressure tool being rotatable about the pressure tool axis, the pressure tool being also rotatable about the bending form axis.

20 Claims, 3 Drawing Sheets

ACETABULAR REAMER LIPPING SYSTEM AND METHOD

BACKGROUND OF THE INVENTION

1. Field of the Invention

The present invention relates to a lipping tool for lipping an acetabular reamer, and, more particularly, to a lipping tool and method that can be used on a range of sizes of acetabular reamers.

2. Description of the Related Art

A hip joint prosthesis requires preparation of the acetabulum by milling a precision shape therein using an acetabular reamer. A typical acetabular reamer has a hollow hemispherical shell shape with apertures in the hemispherical shell. The hemispherical shell is attached to a shaft which can be inserted into a rotating tool such as a drill thereby providing rotation of the acetabular reamer, and hence, the motive force for the milling operation. The apex of the hemispherical shell typically is along the shaft longitudinal axis.

The apertures in the hemispherical shell have a dual purpose. Firstly, an edge of each aperture is formed outwardly, respective to the shell center, to form a cutting tooth or cutting surface. The forming of the aperture edge outwardly is referred to as a lipping operation. Secondly, the apertures allow milled tissue to collect in the shell interior, thereby providing a somewhat self-cleaning aspect to the milling operation. The apertures and cutting surfaces are located on the shell to provide approximately 180° cutting coverage during rotation of the acetabular reamer thereby allowing a uniform milling of the acetabulum.

Variation in the size of the acetabulum for the human population requires a range of sizes of acetabular reamers, a specific size of the acetabular reamer being determined by the hip joint size of the person undergoing hip joint prosthesis. The different sizes of acetabular reamers is generally specified by different radii of curvature, or diameters, of the hemispherical shell.

A known type of acetabular reamer is sometimes referred to as a "cheese grater" style which looks like a hemispherical cheese grater with typically circular apertures therein. A portion of the circumference of each aperture is lipped outwardly forming cutting surfaces or cutting teeth, and having a peak therein. There are at least three problems with this style of reamer. Firstly, the hemispherical cut in the acetabulum produced by the peaked teeth can be rough. Secondly, the cheese grater style reamer with peaked teeth cuts poorly at the apex of the acetabular reamer. Thirdly, a large number of these relatively small teeth are required to ensure complete 180° cutting coverage during rotation of the acetabular reamer thereby allowing a uniform milling of the acetabulum. Past attempts to make acetabular reamers with longer non-peaked cutting teeth, to overcome the problems stated above, have required frequent manufacturing setups.

One of the challenges associated with manufacturing an acetabular reamer is the setup, or changeover, time required for the lipping operation. Setup generally includes a change in tooling, materials and/or operating parameters for a machine used in a given manufacturing operation. A specific machine may be used to perform the lipping operation on a variety of acetabular reamer sizes. Given past methods of lipping the cutting surfaces, particularly relatively long non-peaked cutting surfaces, and the different radii of curvature for different sizes of acetabular reamers, a setup was required when a machine prepared for use with a different acetabular reamer size than was just previously lipped on that machine. Setup is inherently lost productive time for a lipping operation in that no lipping of acetabular reamers can occur during setup.

What is needed in the art is tooling and a method for lipping cutting surfaces on a range of acetabular reamer sizes that can lip relatively long cutting surface in a non-peaked manner, reduces or completely eliminates setup time for a lipping operation and thereby maximizes productive time on a machine used for a lipping operation, reduces manufacturing costs per reamer, increases reamer manufacturing throughput and increases the return on investment for a machine and tooling used for lipping.

SUMMARY OF THE INVENTION

The present invention provides a lipping tool and method for lipping acetabular reamer cutting surfaces that can be used for a variety of acetabular reamer sizes.

The invention comprises, in one form thereof, a lipping tool for lipping an acetabular reamer, the lipping tool comprising a bending form having a bending form curved surface and a bending form axis of rotation; and a pressure tool having a pressure tool curved surface adjacent to and complimentary with the bending form curved surface. The pressure tool has a pressure tool axis. The pressure tool is rotatable about the pressure tool axis, and the pressure tool is also rotatable about the bending form axis.

An advantage of the present invention is the same tooling and method can be used for a variety of different sizes of acetabular reamers, thereby eliminating lipping setup time or changeover due to lipping a different size of acetabular reamer than was manufactured just previously on the same machine.

Another advantage of the present invention is the ability to lip a relatively long cutting surface.

Another advantage of the present invention is the ability to lip a uniform or non-peaked cutting surface.

Another advantage of the present invention is maximization of productive time on a machine used for a lipping operation.

Yet another advantage of the present invention is the reduction in manufacturing costs per reamer.

Yet another advantage of the present invention is the increase in reamer manufacturing throughput.

A further advantage of the present invention is the increase of return on investment for a machine and tooling used for lipping acetabular reamers.

A yet further advantage of the present invention is the improved quality of acetabular reamers due to the reduction of recalibration of lipping tool/machine/method combination due to size setup and associated scrap therewith, and minimization of the statistical variation in reamer lipping operation.

An even yet further advantage of the present invention is the lipping operation is more independent of highly skilled setup personnel.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 1:
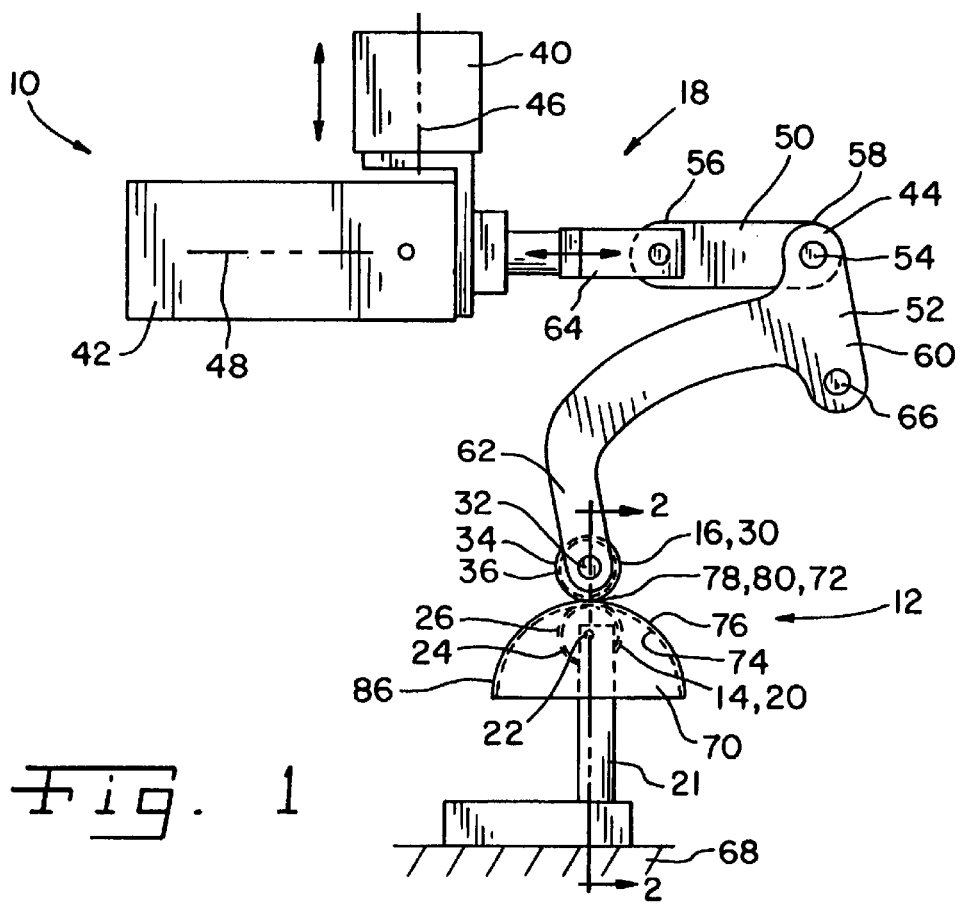
FIG. 1 is a side view of an embodiment of the system for lipping an acetabular reamer of the present invention shown in a first stage of actuation.

Referring now to the drawings, and more particularly to FIG. 1, there is shown a system 10 for lipping an acetabular reamer which generally includes lipping tool 12 and actuator 18. Lipping tool 12 generally includes bending form 14 and pressure tool 16.

Bending form 14 includes bending form curved surface 20 which can extend around the entire periphery of bending form 14 or which can be partially circumferential. Bending form 14 is shown as having a circular profile; however, bending form 14 can have other profiles including various combinations of curved and straight segments. Bending form 14 further includes bending form axis 22. Bending form 14 can be fixed with respect to bending form axis 22 or can rotate about bending form axis 22. Bending form 14 can include an at least partially circumferential bending protrusion 26 at bending form curved surface 20 and can also include at least one at least partially circumferential compression flange 24 adjacent bending protrusion 26. Bending protrusion cross-section 28 (FIG. 2) is shown as having an approximately triangular cross-section; alternatively, bending protrusion cross-section 28 can have a cross-section with at least one curved segment. Bending form 14 can include mount 21, or alternatively, mount 21 and bending form 14 can be of single piece or unitary construction.

Pressure tool 16 includes pressure tool curved surface 30 which can extend around the entire periphery of pressure tool 16 or which can be partially circumferential. Pressure tool 16 is shown as having a circular profile, however, pressure tool 16 can have other profiles including various combinations of curved and straight segments. Pressure tool 16 further includes pressure tool axis 32. Pressure tool 16 can be fixed with respect to pressure tool axis 32 or can rotate about pressure tool axis 32. Pressure tool 16 rotates about bending form axis 22. Pressure tool 16 can include an at least partially circumferential bending recess 36 at pressure tool curved surface 30 and can also include at least one at least partially circumferential compression flange 34 adjacent bending recess 36. Bending recess cross-section 38 (FIG. 2) is shown as having an approximately triangular cross-section; alternatively, bending recess cross-section 38 can have a cross-section with at least one curved segment. Pressure tool curved surface 30 is complimentary with bending form curved surface 20.

Actuator 18 includes press ram 40, hydraulic or pneumatic cylinder 42 and pivoting linkage 44. Press ram 40 includes press ram longitudinal axis 46 in the same direction as the motion (arrows) of press ram 40. Cylinder 42 includes cylinder axis 48 and cylinder rod 64 having a motion (arrows) in the same direction as cylinder axis 48. Pivoting linkage 44 includes first stage 50, second stage 52 and pivot 54 therebetween. First longitudinal end 56 of first stage 50 connects to cylinder 42 at cylinder rod 64. Second longitudinal end 58 of first stage 50 connects to pivot 54. Second stage 52 of pivoting linkage 44 includes first end 60, anchor point 66 and second end 62. First end 60 of second stage 52 pivotably connects to pivot 54 and second end 62 of second stage 52 rotatably connects to pressure tool 16. Anchor point 66 can be anchored to press ram 40. Actuator 18 can also include press table 68 or some other suitable structure.

Figure 3:
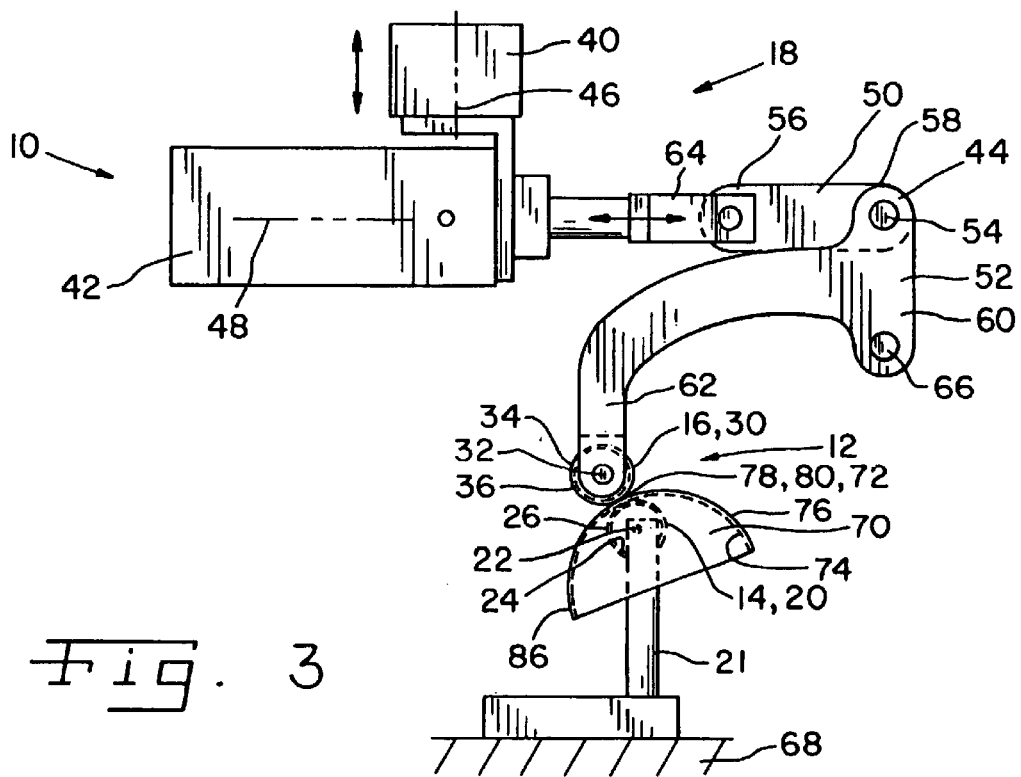
FIG. 3 is a side view of the system of FIG. 1 shown in a second stage of actuation.
Figure 2:
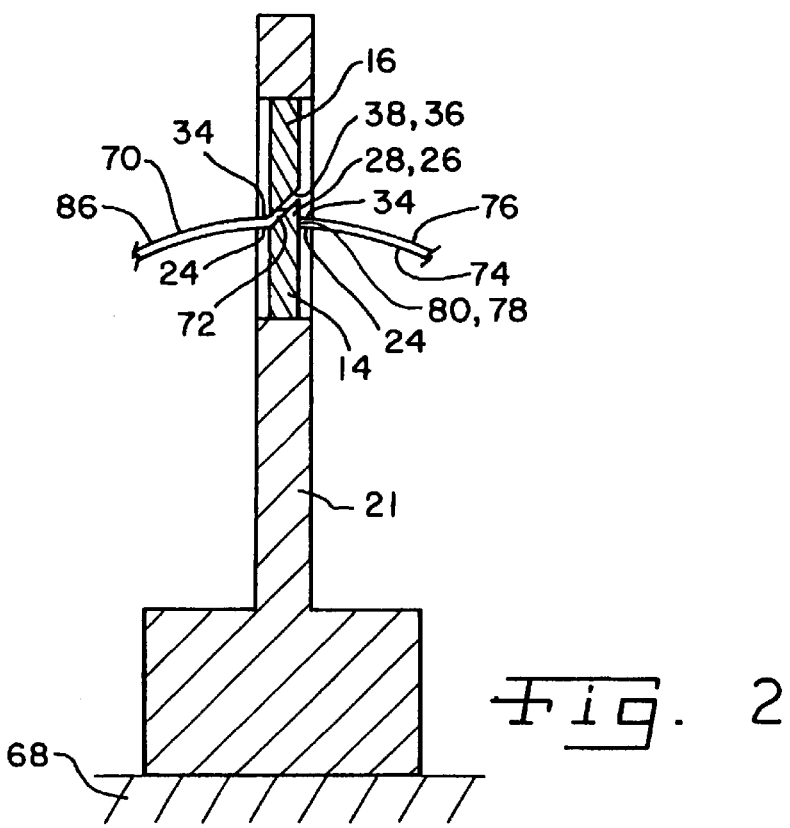
FIG. 2 is a section view of the system of FIG. 1 taken along section line 2—2 emphasizing the pressure tool, acetabular reamer and bending form interaction detail.
Figure 4:
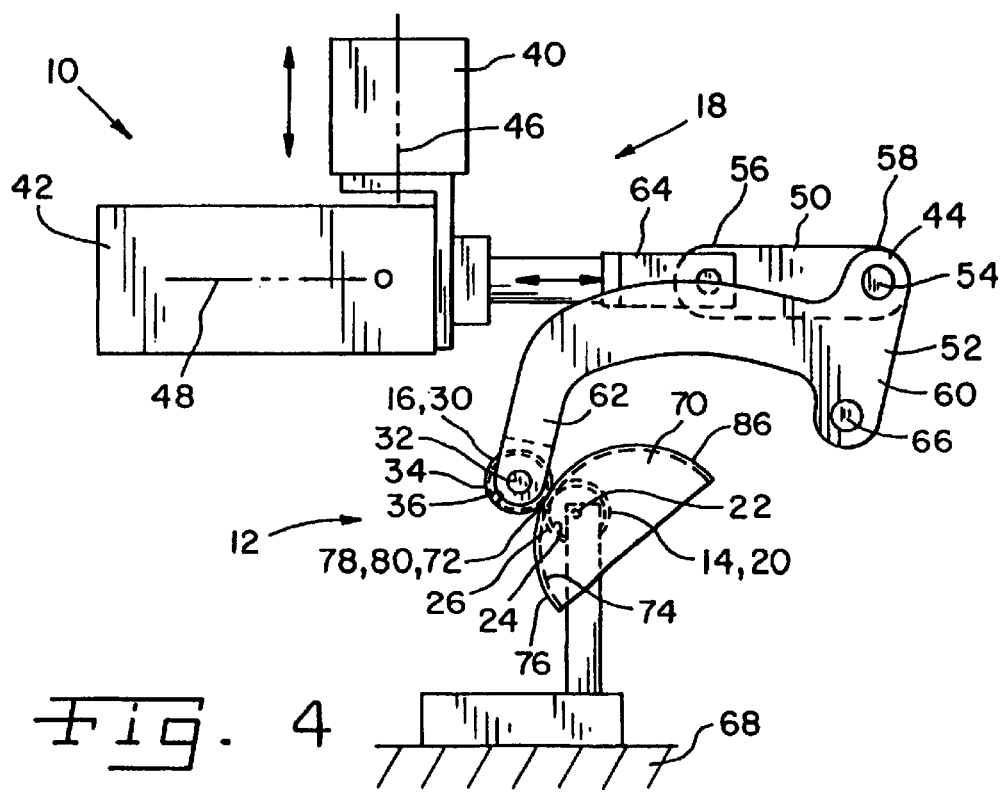
FIG. 4 is a side view of the system of FIG. 1 shown in a third stage of actuation.

In use, bending form 14 is mounted on press table 68 or some other suitable structure. First side 74 of acetabular reamer 70 is placed on bending form 14 in region 78 of cutting tooth 72. An aperture, shown in part at 80, is suitably manufactured in acetabular reamer 70. Region 78 typically corresponds to the cutting surface of cutting tooth 72. Actuator 18 actuates pressure tool 16 to contact second side 76 of acetabular reamer 70 at region 78 with pressure tool 16. This state of the process is shown in FIGS. 1 and 2 and pressure tool curved surface 30 is adjacent to and complimentary with bending form curved surface 20, and remains as such through the completion of the lipping operation. Press ram 40 actuates downward (FIG. 3), thereby pressing acetabular reamer 70 between bending form 14 and pressure tool 16 at a portion of region 78, and bending the portion initiating the outward shaping or lipping of cutting tooth 72. As further shown in FIGS. 3 and 4, downward actuation of press ram 40 extends rod 64, with the combined action of press ram 40, rod 64 and first stage 50 pivoting second stage 52 about pivot 54 and hence rolling acetabular reamer 70 between bending form 14 and pressure tool 16 through a remaining region 78 of cutting tooth 72, thereby bending the remaining region 78 of cutting tooth 72.

Cutting tooth 72 can thereby be lipped an approximately uniform height above second side 76. However, peaked cutting teeth can also be formed by suitable modifications to bending form 14 and pressure tool 16.

During the lipping operation, pressure tool 16 is rotated about bending form axis 22 and can also be rotated about pressure tool axis 32. Bending form 14 can also be rotated about bending form axis 22 during the lipping process.

Figure 5:
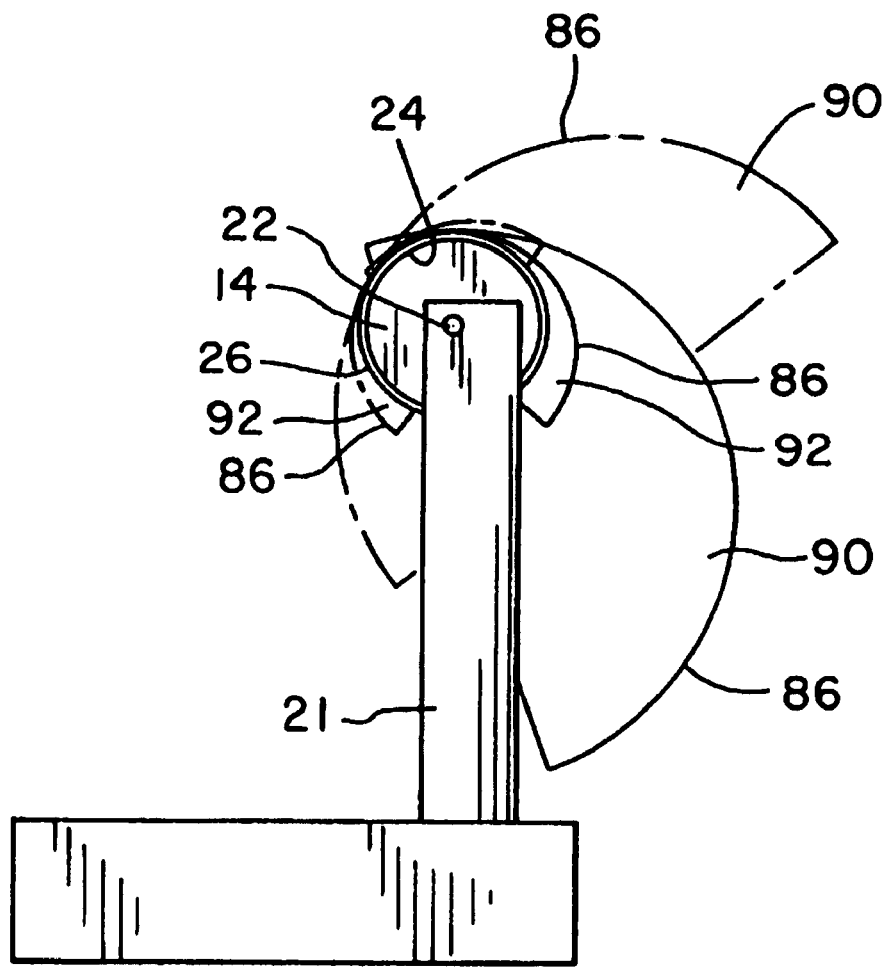
FIG. 5 is a side view of an embodiment of the bending form and acetabular reamer detail demonstrating how different size acetabular reamers can be lipped at different locations on the respective hemispherical shell.

FIG. 5 demonstrates how a single lipping tool 12 (showing only bending form 14 in FIG. 5) can be used for a relatively large radius of curvature acetabular reamer 90 and a relatively small radius of curvature acetabular reamer 92. Also demonstrated in FIG. 5 is how a single lipping tool 12 can be used to lip cutting teeth located at different locations along the curved portion 86 of either reamer 92 or reamer 90 or any size therebetween. As long as the cutting teeth on the different size reamers are the same length the lipping operation will subtend a constant arc length and can be used for different size reamers without a setup change. However, the present invention does not inherently require a fixed cutting tooth length for different sized reamers and can be used for a variety of cutting tooth lengths without setup change by appropriately adjusting the rotation of the pressure tool.

Alternatively, bending form curved surface 20 can have bending recess or die 36 and pressure tool curved surface 30 can have bending protrusion or punch 26. In this alternative form acetabular reamer 70 is rotated so that, during the lipping operation, first side 74 is in contact with pressure tool 16 and second side 76 is in contact with bending form 14.

The present invention can be used with other shapes of acetabular reamers such as partially hemispherical reamers and dome topped cylinders, and can even be used on flat shapes.

A typical range of sizes of acetabular reamer 70 may have radii of curvature from approximately 10 mm to 50 mm, although the present invention is not limited to use within this range. There is no upper limit of acetabular reamer sizes that can be used with the present invention. Likewise, by suitably reducing the radii of curvature for bending form curved surface 20 and pressure tool curved surface 30, there is no inherent lower limit on the size of acetabular reamer which can be lipped with the present invention.

A typical range for a length of cutting tooth is approximately 1 mm to 25 mm, although the present invention is not limited to use within this range. Similarly as with reamer sizes, there is no inherent upper or lower limit on the length of cutting tooth that can be lipped with the present invention, given suitable modifications, when necessary, within the scope of the present invention.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A lipping tool for lipping an acetabular reamer, said lipping tool comprising:
   a bending form having a bending form curved surface and a bending form axis; and
   a pressure tool having a pressure tool curved surface adjacent to and complimentary with said bending form curved surface, said pressure tool having a pressure tool axis, said pressure tool being rotatable about said pressure tool axis, said pressure tool being rotatable about said bending form axis.

2. The lipping tool of claim 1, wherein said bending form is rotatable about said bending form axis.

3. The lipping tool of claim 1, further including at least one at least partially circumferential compression flange on at least one of said bending form and said pressure tool.

4. The lipping tool of claim 1, further including an at least partially circumferential bending protrusion at said bending form curved surface and an at least partially circumferential bending recess at said pressure tool curved surface, at least one of said at least partially circumferential bending protrusion and said at least partially circumferential bending recess having one of an approximately triangular cross-section and a cross-section with at least one curved segment.

5. A system for lipping an acetabular reamer, said system comprising:
   a bending form having a bending form curved surface and a bending form axis;
   a pressure tool having a pressure tool curved surface adjacent to and complimentary with said bending form curved surface, said pressure tool having a pressure tool axis; and
   an actuator connected to said pressure tool for effecting rotation of said pressure tool about said pressure tool axis and about said bending form axis.

6. The lipping tool of claim 5, wherein said bending form is rotatable about said bending form axis.

7. The lipping tool of claim 5, further including at least one at least partially circumferential compression flange on at least one of said bending form and said pressure tool.

8. The lipping tool of claim 5, further including an at least partially circumferential bending protrusion at said bending form curved surface and an at least partially circumferential bending recess at said pressure tool curved surface, at least one of said at least partially circumferential bending protrusion and said at least partially circumferential bending recess having one of an approximately triangular cross-section and a cross-section with at least one curved segment.

9. The lipping tool of claim 5, wherein said actuator includes a press ram, one of a hydraulic and a pneumatic cylinder, and a pivoting linkage, said press ram connected to said cylinder, said cylinder connected to said pivoting linkage, said pivoting linkage connected to said pressure tool.

10. The lipping tool of claim 9, wherein said press ram includes a press ram longitudinal axis, said cylinder includes a cylinder axis, said press ram connected to said cylinder with said press ram axis approximately orthogonal to said cylinder axis.

11. The lipping tool of claim 9, wherein said pivoting linkage includes a first stage, a second stage and a pivot therebetween, said first stage includes a first longitudinal end and a second longitudinal end, said first longitudinal end connected to said cylinder, said second longitudinal end connected to said pivot, said second stage includes a first end and a second end, said first end pivotably connected to said pivot, said second end rotatably connected to said pressure tool.

12. The lipping tool of claim 9, wherein said pivoting linkage is also connected to said press ram.

13. A method of lipping an acetabular reamer including at least one cutting tooth, including the steps of:
   providing a bending form and a pressure tool;
   placing a first side of the acetabular reamer in a region of at least one cutting tooth on said bending form;
   contacting a second side of the acetabular reamer at said region with said pressure tool;
   pressing the acetabular reamer between said bending form and said pressure tool at a portion of said region thereby bending said portion; and
   rolling the acetabular reamer between said bending form and said pressure tool through a remaining region of said cutting tooth thereby bending said remaining region of said cutting tooth.

14. The method of claim 13, wherein said rolling step includes rotation of said pressure tool about a pressure tool axis and about a bending form axis.

15. The method of claim 14, wherein said rolling step includes rotating said bending form about a bending form axis.

16. The method of claim 13, wherein said method is carried out using the acetabular reamer with a curved portion, said curved portion having a radius of curvature varying from approximately 10 mm to 50 mm.

17. The method of claim 16, wherein said rolling step subtends an arc length of said curved portion, said arc length is constant and independent of said radius of curvature.

18. The method of claim 16, wherein said rolling step subtends an arc length of 1 mm to 25 mm.

19. The method of claim 16, wherein said method is carried with said curved portion being a hemisphere.

20. The method of claim 13, wherein said cutting tooth is bent an approximately uniform height from said second side.

* * * * *